US007435432B2

(12) United States Patent
Olson (10) Patent No.: US 7,435,432 B2
(45) Date of Patent: Oct. 14, 2008

(54) COMBINED MARINE AND PLANT EXTRACT COMPOSITIONS

(75) Inventor: Bengt Krister Olson, Østerbrogade 56 C, 2. tv 2100 Copenhagen Ø (DK)

(73) Assignee: Bengt Krister Olson, Copenhagen O (DK)

( * ) Notice: Subject to any disclaimer, the term of this patent is extended or adjusted under 35 U.S.C. 154(b) by 0 days.

(21) Appl. No.: 09/853,635

(22) Filed: May 14, 2001

(65) Prior Publication Data

US 2002/0012714 A1    Jan. 31, 2002

(30) Foreign Application Priority Data

May 12, 2000  (DK)  ............................... 2000 00782

(51) Int. Cl.
*A61K 35/32* (2006.01)
*A61K 35/34* (2006.01)
*A61K 36/81* (2006.01)
*A61K 36/87* (2006.01)
*A61K 31/715* (2006.01)

(52) U.S. Cl. ..................... 424/766; 424/777; 424/539; 424/548; 514/54

(58) Field of Classification Search ................. 424/548, 424/766, 54, 464, 539, 777; 514/54
See application file for complete search history.

(56) References Cited

U.S. PATENT DOCUMENTS

| 4,444,752 | A |   | 4/1984  | Prudden |         |
|-----------|---|---|---------|---------|---------|
| 5,569,458 | A | * | 10/1996 | Greenberg |       |
| 5,906,811 | A | * | 5/1999  | Hersh   | 424/54  |
| 6,630,163 | B1 | * | 10/2003 | Murad   | 424/464 |

FOREIGN PATENT DOCUMENTS

| EP | 0659402 |   | 6/1995 |
|----|---------|---|--------|
| EP | 0715852 |   | 6/1996 |
| JP | 09241637 |  | 9/1997 |
| WO | WO 00/07607 | * | 2/2000 |

OTHER PUBLICATIONS

Johnson, T., 1999, CRC Ethnoboany Desk Reference, CRC Press LLC, Boca Raton, FL., U.S.A., p. 499, col. 2, entry 16162.*
Duke, J. et al. Handbook of Medicinal Herbs, 2002, CRC Press, Boca Raton, FL., U.S.A., p. 502.*
Spraycar (, M. (editor). Stedman's Medical Dictionary. 1995. Williams and Wilkins, Baltimore, p. 1134, col. 2, Lines 9-14.*
Journal of Dermatological Sciences 16 (1998) 226-230 Short communication Modulation of UVA light-induced oxidative stress by B-carotene, lutein and astaxanthin in cultured fibroblasts: Irene O'Connor and Nora O'Brien.
Innovations Forum Life Science News 6, 2000, Amersham Pharmacia Biotech, pp. 26 & 27 Novel activity assays for the collagenases MMP-1 and MMP-13 M. Sully et al.
Pathophysiology Of Premature Skin Aging Induced By Ultraviolet Light The New England Journal Of Medicine vol. 337, No. 20 (1997), pp. 1419-1428 Gary J. Fisher et al.
The Society for Investigative Dermatology, Inc. Molecular Mechanisms of Photoaging and its Prevention by Retinoic Acid: Ultraviolet Irradiation Induces MAP Kinase Signal Transduction Cascades that Induce Ap-1-Regulated Matrix Metalloproteinases that Degrade Human Skin In Vivo, vol. 3, No. 1, Aug. 1998, pp. 61-68 Gary J. Fisher.
British Journal of Dermatology 2000: 142: 267-273 Histological increase in inflammatory infiltrate in sun-exposed skin of female subjects: the possible involvement of matrix metalloproteinase-1 produced by inflammatory infiltrate on collagen degradation T. Hase et al.
Experimental Dermatology 1993: 2: 92-97 UVA irradiation stimulates the synthesis of various matrix-metalloproteinases (MMP's) in cultured human fibroblasts G. Herrmann et al.
The Society for Investigative Dermatology, Inc., vol. 99, No. 4, Oct. 1992, pp. 440-444 Ultraviolet A Irradiation Stimulates Collagenase Production in Cultured Human Fibroblasts Marta J. Petersen et al.
Photochemistry and Photobiology, vol. 62, No. 3, pp. 444-448, 1995 Regulation and Inhibition of collagenase expression by long-wavelength ultraviolet radiation in cultured human skin fibroblasts Marta J. Petersen et al.
Arch of Dermatol Research (1991) 283:506-511 UVA irradiation induces collagenase in human dermal fibroblasts in vitro and in vivo K. Scharffetter et al.
The Society for Investigative Dermatology, Inc., vol. 104 No. 2, Feb. 1995, pp. 194-198 Singlet Oxygen May Mediate the Ultraviolet A-Induced Synthesis Of Interstital Collagenase Meinhard Wlaschek et al.
Exp Dermatology 1997: vol. 6: pp. 199-213 Matrix metalloproteinases in skin Kähäri et al.
Federation of European Biochemical Societies, 1991: vol. 289, pp. 1, 4-7, The origin of matrix metalloproteinases and their familial relationships George J. P. Murphy et al.
Critical Reviews in Oral Biology and Medicine, 3(4):353-370 (1992) The Cultured Diploid Fibroblast as a Model for the Study of Cellular Aging Thomas H. Norwood and William R. Pendergrass.
Biochemical and Biophysical Research Communications, vol. 201, No. 2, 1994, pp. 665-672 Kinetin Delays The Onset Of Ageing Characteristics In Human Fibroblasts Suresh I. S. Rattan and Brian F. C. Clark.

(Continued)

*Primary Examiner*—Jon P Weber
*Assistant Examiner*—Kailash C. Srivastava
(74) *Attorney, Agent, or Firm*—Roberts, Mlotkowski, Safran & Cole, P.C.

(57) ABSTRACT

A composition comprising cartilage extract, grape seed extract and tomato extract was found to have remarkable anti-oxidant effect and free-radical inhibition. The tomato extract comprises lycopene. The composition which comprises a hydrophilic antioxidant, a lipophilic (hydrophobic) antioxidant, and a cartilage extract dramatically increases collagen synthesis in the dermis. Furthermore, the composition lowers collagenase activity and levels of advanced glycation end products (AGE). The signs of ageing, such as photoageing due to exposure to UV radiation, are related to the levels of collagen syntheses and free-radical oxidation. Compositions of the invention are intended for the treatment of ageing skin and the delaying of the onset of the signs of ageing in healthy skin.

40 Claims, 4 Drawing Sheets

OTHER PUBLICATIONS

Journal of Ethnopharmacology 43 (1994) 125-133 Testing garlic for possible anti-ageing effects on long-term growth characteristics, morphology and macromolecular synthesis of human fibroblsts in culture Lise Svendsen, Suresh I. S. Rattan and Brian F. C. Clark.

Scientific American Biology_Aging (Jul. 2000), AGE Breakers—Rupturing the body's sugar-protein bonds might turn back the clock Lisa Melton.

Proc. Natl. Acad. Sci. USA, vol. 93, Biochemistry, pp. 485-490, 1996 Longevity and the genetic determination of collagen glycoxidation kinetics in mammalian senescene David R. Sell et al.

Diabetes, vol. 41, Suppl. 2, 1992, pp. 42-48 Role of Oxygen in Cross-Linling and Chemical Modification of Collagen by Glucose Min-Xin Fu et al.

Biochimica et Biophysica Acta 1428 (1999) 45-56, Elsevier Generation of active oxygen species from advanced glycation end-products (AGEs) during ultraviolet light A (UVA) irradiation and a possible mechanism for cell damaging Hitoshi Masaki, Yuri Okano and Hiromu Sakurai.

Photodermatology Photoimmunology & Photomedicine, 1995:11:192-197 Effects of ultraviolet A and antioxidant defense in cultured fibroblasts and keratinocytes A. Moysan et al.

* cited by examiner

MMP1 levels

Day 1

Figure 2b

MMP1 levels

Day 4

Figure 3

AGE concentration - day 1

Figure 4

COMBINED MARINE AND PLANT EXTRACT COMPOSITIONS

This application claims priority to Danish Application PA 2000 00782, filed May 12, 2002.

FIELD OF THE INVENTION

The present invention concerns compositions for oral use, said compositions containing cartilage or compounds extractable from cartilage as well as hydrophilic and lipophilic antioxidants.

BACKGROUND OF THE INVENTION

Free radicals are formed in the body, e.g. in the skin, as a result of UV radiation, pollution, alcohol, etc. Excess of free radicals can cause severe damage to tissue structure, including skin structure, and thus signs of ageing begin to appear.

There has therefore been made use of antioxidants, both hydrophilic and lipophilic in combination, in reducing the oxidative stress caused by free radicals in the skin (Maffei Facino et al. ("Free Radical Scavenging and Anti-enzyme Activities of Procyanidines from *Vitis vinifera*" Arzneim.-Forsch./Drug Res., 44(1), Nr. 5 (1994), pp 592-601).

U.S. Pat. No. 5,648,277 discloses oral formulations comprising both hydrophilic and lipophilic antioxidants.

JP 09 241637 discloses compositions comprising an active free-radical scavenger and uronic acids or mucopolysaccharides.

It has also been established that the administration of protein complexes containing mucopolysaccharides derived from marine cartilage sources have the ability to improve the texture of the dermis of the skin by making it more dense and firm (Kieffer M E, Efsen J., *J. Eur. Acad. Dermatol. Venereol.*, 1998 September; 11(2):129-136).

SUMMARY OF THE INVENTION

The present investigators have found that the unique combination of a cartilage extract with a special blend of plant extract results in a surprisingly effective composition for increasing collagen synthesis in the skin as well as reducing to a remarkable level the radical mediated oxidation within the dermis. A decrease in collagen synthesis and radical oxidation are both associated with the ageing process in the skin.

In a first aspect, the invention relates to a composition for oral administration comprising plant extract and cartilage extract wherein the plant extract comprises grape seed extract and tomato extract.

The invention may be alternatively defined as a composition for oral administration comprising plant extract and cartilage extract wherein the plant extract comprises grape seed extract and lycopene in a weight/weight ratio of about 5:1 to 15:1, preferably about 10:1.

A further aspect of the invention relates to a composition for oral administration, said composition comprising i) cartilage, one or more compounds extractable therefrom, or derivatives thereof; ii) one or more hydrophilic antioxidants; and iii) one or more lipophilic antioxidants; wherein said composition increases collagen synthesis by at least 35% in a cell model.

A composition as defined herein for the general maintenance of healthy skin, to delay the onset of the degeneration of skin due to ageing or UV exposure, and for the treatment of the signs of ageing in skin is a still further aspect of the invention.

DETAILED DESCRIPTION OF THE INVENTION

In the context of the present invention, the term "hydrophilic" as applied to the hydrophilic antioxidant generally means that the antioxidant is sufficiently soluble in, and hence able to function in, an aqueous medium in the body. In the present context, an antioxidant is considered to be hydrophilic if it has a solubility in water of above 0.05 g per 100 g of water. A hydrophilic antioxidant preferably has a solubility in water of above 0.5 g, more preferably above 1 g, in particular above 5 g, more particularly above 10 g, most particularly above 25 g, especially above 50 g, such as above 100 g per 100 g of water.

Similarly, the term "lipophilic" as applied to the lipophilic antioxidant generally means that it is sufficiently soluble in, and hence able to function in, a lipid medium in the body. This also means that it has a very low solubility in water. In the present context, an antioxidant is considered to be lipophilic if it has a solubility in water of below 0.05 g per 100 g of water. A lipophilic antioxidant preferably has a solubility in water of below 0.005 g, in particular below 0.0005 g per 100 g of water.

The term "cartilage extract" is intended to include cartilage, components that may be extracted therefrom, and derivatives thereof, including synthetic forms of compounds extractable from cartilage and synthetically prepared derivatives. Compounds termed "cartilage extract" may also be found in other tissue containing connective tissue, e.g. skin or hide, and may be extracted therefrom. The cartilage may be selected from the group consisting of marine animal cartilage, fish cartilage, mollusc cartilage and land-dwelling mammal cartilage. Marine animals may be selected from the group consisting of a whale, dolphin and seal; the fish may be selected from the group consisting of shark, salmon, tuna, cod and other known fish; the mollusc may be a squid; and land-dwelling mammal may be selected from the group consisting of a bovine, porcine, chicken, duck and turkey. The cartilage or extracts therefrom are preferably selected from bovine cartilage, porcine cartilage, shark cartilage, squid cartilage, chicken cartilage and salmon cartilage, and extracts therefrom.

Cartilage itself may be used. It may typically be used in the form of dried, e.g. lyophilised, comminuted cartilage. Useful extracts of the above mentioned types of cartilage or other tissue containing the appropriate components may typically be prepared through partial enzymatic proteolytic hydrolysis of cooked tissue followed by filtration and drying of the hydrolysate, e.g. through spray drying or lyophilisation. Such extracts have the advantage of being partially or fully soluble in aqueous media. (prepared according to U.S. Pat. No. 3,862,003)

The cartilage extract typically comprises of one or more compounds extractable from cartilage, and preferably comprises glycosaminoglycans, optionally bound to a peptide. The cartilage extract preferably comprises chondroitin sulphate, keratan sulphate, hyaluronic acid, or dermatan sulphate or mixtures thereof. The term "cartilage extract" is intended to include compounds obtainable from cartilage but the compounds may actually be obtained from other sources. A particularly preferred source of cartilage extract is shark cartilage.

The term "cartilage extract" may relate to compounds extractable from cartilage or derivatives thereof. As stated, the cartilage extract may come from other natural sources but may be from a synthetic source, i.e. synthetically or semi-synthetically prepared. Preferably, the cartilage extract is extracted from natural source, most preferably, the extract is extractable from cartilage, particularly preferably the extract is extracted from cartilage.

As stated, the invention relates in a first aspect to a composition for oral administration comprising plant extract and cartilage extract wherein the plant extract comprises grape seed extract and tomato extract in a weight/weight ratio of about 2:1 to 1:2, preferably about 1:1. The present investigators have found that the unique combination of a cartilage extract with a special blend of plant extract resulted in a surprisingly effective composition for increasing collagen synthesis in the skin as well as reducing to a remarkable level the UV radiation and oxidative stress, such as radical oxidation, related to the degradative process within the dermis.

The beneficial effects of a combination of grape seed extract and tomato extract as antioxidants were unexpectedly dramatically improved by the addition of cartilage extract. The results were surprisingly in part since cartilage extract has no antioxidant activity of its own.

Typically, the cartilage extract and the plant extract are present in a weight/weight ratio of about 1:2 to 2:1, preferably about 1:1.

The cartilage extract preferably comprises glycosaminoglycans selected from the group consisting of a chondroitin ester, a keratan ester, hyaluronic acid or an ester thereof, a dermatan ester, heparin, a heparan ester. These may be bound to a protein or peptide or as epimeric or polymeric forms of chondroitin ester, a keratan ester, hyaluronic acid or an ester thereof, a dermatan ester, heparin, a heparan ester, preferably chondroitin sulphate, keratan sulphate, hyaluronic acid or an ester thereof, a dermatan sulphate, a heparin, a heparan sulphate The glycosaminoglycans may be selected from the group consisting of chondroitin-4-sulphate, chondroitin-6-sulphate, and keratan sulphate, each of which may be optionally bound to a peptide. Most preferably, the composition of the present invention comprises cartilage extract comprising chondroitin sulphate, optionally bound to a peptide.

In a typical embodiment of the present invention wherein the cartilage extract comprises 5-100% w/w of chondroitin sulphate.

In a preferred embodiment, the composition of the present invention comprises less than 1% weight/weight collagen, preferably less than 0.5%, particularly preferably less than 0.1% collagen protein. In the typical manner collagen extract is prepared, it does not comprise collagen to any appreciable amount. The extract is preferably prepared through enzymatic proteolytic hydrolysis thus digesting collagen proteins into peptides. The composition comprising this extract having this low collagen level exhibited the unexpected beneficial effects. Consequently, collagen or a source thereof is preferably not further added to the composition of the present invention. In a most preferred embodiment, the composition is essentially collagen-free.

Similarly, a composition of the present invention typically comprising less than 0.025% beta-carotene, preferably less than 0.02% beta-carotene, particularly less than 0.01% beta-carotene. Thus, a further aspect of the invention relates to a composition that can achieve the beneficial effects as described infra with very little or essentially no beta-carotene.

Conversely, the current understanding is that the lycopene content, relatively or absolutely, is particularly important to the unexpected beneficial effects of the composition of the present invention. The plant extract, specifically the tomato extract, comprises lycopene. Preferably, the tomato extract comprises about 5 to 12%, typically approximately 10% lycopene, weight/weight. The tomato extract may be from a single or a blend of tomatoes.

In a typical embodiment, the tomato which is used to prepare the tomato extract is *Lycopersicurn aesculentum*, thereby providing suitable absolute and relative levels of lycopene.

In a preferred embodiment of the present invention, the composition comprises 0.1 to 5% of lycopene weight/weight, preferably 0.2 to 4% lycopene, such as 0.3 to 2% lycopene, most preferably 0.3 to 1% lycopene, particularly 0.3 to 0.8%, such as 0.3 to 0.6% lycopene.

In an alternative definition of the composition of the present invention, the composition comprises a plant extract and a cartilage extract wherein the plant extract comprises grape seed extract and lycopene in a weight/weight ratio of about 5:1 to 15:1, preferably about 10:1. As stated, lycopene in said ratio is, according to the current understanding of the invention, of significant importance for achieving the surprising beneficial antioxidant effect.

In a suitable embodiment, the antioxidant activity $IC_{50}$ of the lipophilic antioxidant is lower than $1.2 \times 10^{-7}$ for scavenging R./ROO. radicals in lipid peroxidation of an unsaturated phospholipid in an aqueous medium. Typically, the lipophilic antioxidant exhibiting an antioxidant activity $IC_{50}$ of at most $1.2 \times 10^{-7}$ for scavenging R./ROO. radicals in lipid peroxidation of an unsaturated phospholipid in an aqueous medium is the carotenoid compound lycopene (also termed ψ,ψ-carotene). Lycopene may typically be obtained by extraction from certain fresh fruits such as tomatoes, water melon, red grapefruit or guava fruit in a manner known per se, or it may be prepared synthetically in a known manner.

The beneficial effects of the oral composition of the present invention is the result of the novel combination of three components: cartilage extract, grape seed extract and tomato extract. Grape seed extract provides hydrophilic antioxidants. Tomato extract provides lipophilic antioxidants. The invention thus relates to a novel combination of antioxidants with compounds extractable from cartilage. A further aspect of the present invention thus relates to a composition for oral administration, said composition comprising i) cartilage, one or more compounds extractable therefrom, or derivatives thereof; ii) one or more hydrophilic antioxidants, and iii) one or more lipophilic antioxidants; wherein said composition increases collagen synthesis by at least 35% as determined by Test Method A.

Collagen synthesis decreases notably in aged skin cells. The decrease of collagen in skin results in a change in texture and rheological features of the skin, and the typical signs of ageing such as wrinkles, decreased smoothness, loss of elasticity and firmness.

As shown in Example 2, the composition of the present invention resulted in a surprisingly dramatic increase in collagen synthesis, in comparison to other combinations and individual components. The synthesis of collagen was evaluated by measuring the incorporation of radioactive proline ([$^{14}$C]-Proline) into proline-containing proteins, which are mostly regarded to be collagen, wherein 30% of the total number of amino acids are proline.

Dermal skin fibroblasts cultured in medium containing a combination of grape seed (G) extract and tomato (T) extract, GT (as disclosed in U.S. Pat. No. 5,648,277), resulted in a decrease in the degree of incorporation of proline compared to the control: 3.6% incorporation compared with 4.8% in the control, a 25% decrease. Cell cultures containing a combination fish (F) extract and tomato (T) extract, FT, had no significant influence on the proline incorporation, since the degree of incorporation was 5.0% compared with 4.8% in the control, a 4% increase, only. Cell cultures containing a combination of fish (F) and grape seed (G) extract, FG, resulted in a small increase in the degree of incorporation of proline: 5.5% incorporation, a 10% increase compared to the control. Cell cultures containing the only the fish (F) extract resulted in an increase in the degree of incorporation of proline: 6.2% incorporation, a 29% increase.

Cells cultured with a composition according to the present invention, comprising fish, extract (F), grape seed extract (G), and tomato extract (T), FGT, extracts however, surprisingly resulted in a dramatic 80% increase in proline incorporation: (8.4% of proline incorporated). Given that GT extract resulted in a 25% decrease in collagen synthesis and F extract resulted in a 29% increase in collagen synthesis, an 80% increase in collagen synthesis upon combining F with GT is surprising.

The one or more hydrophilic antioxidants of the compositions of the present invention may be from natural or synthetic sources, preferably natural sources. In a typical embodiment, the natural source is selected from the group consisting of pine bark, *Vitis vinifera, Camelia sinensis, Aesculus hippocastanum, Gingo biloba, Cardus marianum, Vaccinium myrtillus, Silybum marianum*.

In a suitable embodiment, the one or more hydrophilic antioxidants are extractable from grape seed of *Vitis vinifera*.

The natural source of the one or more hydrophilic antioxidants typically contain up to 25% w/w of catechin, epicatechin and gallic acid; up to 90% w/w of epicatechin dimer, trimer and/or tetramer, and/or gallates thereof; and up to 10% w/w of epicatechin pentamer, hexamer and/or heptamer, and/or gallates thereof.

The one or more hydrophilic antioxidants may be selected from the group consisting of polyphenols and esters thereof; ascorbic acid (vitamin C) and esters thereof; and pharmaceutically acceptable salts thereof. The polyphenols are typically catechins; leucoanthocyanidins and flavanones; flavanins, flavones and anthocyanins; flavonols; flavonolignans; and oligomers thereof.

In a preferred embodiment, the hydrophilic antioxidants is a catechin selected from the group consisting of proanthocyanin A2 and oligomeric procyanidol (OPC), most preferably an oligomeric procyanidol.

Flavonolignans are typically silymarin or one of the components thereof such as silybin, silydianin, silychristin and isosilybin.

In the composition of the invention, the hydrophilic antioxidant is typically one which exhibits an antioxidant activity $IC_{50}$ of at most $5\times10^{-7}$ for scavenging R./ROO. radicals in lipid peroxidation of an unsaturated phospholipid in an aqueous medium.

As stated, a particularly preferred hydrophilic antioxidant is an extract from grape seed, i.e. seeds of *Vitis vinifera*, said extract typically being obtained by extracting grape seeds using organic solvents such as acetone and/or ethyl acetate or the like, evaporating the solvents, re-dissolving the residue in water, and filtering and drying the filtrate, e.g. by spray drying or lyophilisation. In a particularly preferred embodiment, such an extract typically contains up to 25% w/w of catechin, epicatechin and gallic acid; up to 90% w/w of epicatechin dimer, trimer and/or tetramer, and/or gallates thereof; and up to 10% w/w of epicatechin pentamer, hexamer and/or heptamer, and/or gallates thereof.

The one or more lipophilic antioxidants may also be from a natural or synthetic sources, typically a natural source. The lipophilic antioxidant may be a mixture of antioxidants such as an extract from a natural source comprising a complex mixture of lipophilic antioxidants. A suitable natural source for the lipophilic antioxidant is a tomato variety, particularly the *Lycopersicum aesculentum* variety.

The one or more lipophilic antioxidants are typically carotenoids, procarotenoids, tocopherols, phytosterols and ubiquinones. The carotenoids are particularly interesting lipophilic antioxidants and may be selected from the group consisting of α-carotene, β-carotene, γ-carotene, δ-carotene, lycopene (ψ,ψ-carotene), zeaxanthin, cryptoxanthine, lutein, and xanthofyll.

As stated, the carotenoid lycopene is an especially interesting lipophilic antioxidant. The composition of the present invention most preferably comprises lycopene. Extracts serving as sources of lipophilic antioxidant preferably comprise 5-12% lycopene, such as 7-12% lycopene, preferably approximately 10% lycopene. This may typically translate to a composition of the present invention comprising 0.1 to 5% of lycopene weight/weight, preferably 0.2 to 4% lycopene, such as 0.3 to 2% lycopene, most preferably 0.3 to 1% lycopene, particularly 0.3 to 0.8%, such as 0.3 to 0.6% lycopene, weight/weight.

| A natural source of the lipophilic antioxidant preferably comprises | |
|---|---|
| 5-12% | lycopene |
| 1-1.5% | tocopherols |
| 0.05-0.15% | beta-carotene |
| 0.5-0.75% | phytoene |
| 0.5-0.55% | phytofluene; |
| most preferably comprising | |
| 7-12% | lycopene |
| 1-1.5% | tocopherols |
| 0.05-0.15% | beta-carotene |
| 0.5-0.75% | phytoene |
| 0.5-0.55% | phytofluene. |

The source of the one or more lipophilic antioxidants preferably comprises less than 1% beta-carotene, such as less than 0.75%, such as less than 0.5%, preferably less than 0.25%, most preferably less than 0.2%, particularly less than 0.15%. Similarly, a composition of the present invention typically comprises less than 0.025% beta-carotene, preferably less than 0.02% beta-carotene, particularly less than 0.01% beta-carotene. Thus, a further aspect of the invention relates to a composition that can achieve the beneficial effects as described infra with very little or essentially no beta-carotene.

In a typical embodiment, the sole source of the lipophilic antioxidant is provided by the tomato extract. Alternatively, the lipophilic antioxidant is the tomato extract.

In a typical embodiment of the invention, the composition comprises 20-40% cartilage extract, such as 25-35%, preferably 27-35%, such as 30-35% cartilage extract, weight/weight;

1-10% grape seed extract, such as 2-8%, preferably 3-7%, such as 3-5% grape seed extract weight/weight; and 1-10% tomato extract, such as 2-8%, preferably 3-7%, such as 3-5% tomato extract, weight/weight.

A typical composition of the present invention comprises fish extract (F), grape seed extract (G), and tomato extract (T) in a weight ratio of about 5:1:1 to 15:1:1, such as about 10:1:1.

As stated, the composition of the present invention is able to increase collagen synthesis by at least 35% as determined by Test Method A. Preferably, however, use of the composition under the conditions of Test Method A results in an increase in collagen synthesis by at least 40%, such as by at least 45%, such as at least 50%, at least 55%, preferably at least 60%, such as at least 65%, at least 70%, most preferably at least 75%.

Thus, a further aspect of the invention relates to a method of increasing collagen synthesis or lessening the decrease in collagen synthesis in the dermis comprising the oral administration of a composition as defined herein.

The present investigators have found that not only does the novel composition of the present invention result in an increase in collagen synthesis but also has other indicators of its utility for the treatment of ageing or skin exposed to UV radiation. Accordingly, in a suitable embodiment, the composition reduces the harmful effects of free radicals by at least 40% as measured by MMP-1 activity compared to a control under the conditions of Test Method B, such as at least 45%, such as at least 50%. The oxygen free radicals and the harmful effects therefrom are typically due to UV exposure but may result from other environmental, physiological or genetic factors.

The UV-induced overproduction of MMPs is considered to be one of the major causes of photoageing. UV radiation activates dermal cells resulting in overproduction of MMPs, which are enzymes which degrade collagen and other proteins that comprise the dermal extracellular matrix. The dermal degradation (breakdown) is followed by repair that is imperfect. Imperfect repair yields a deficit in the structural integrity of the dermis and it is repeated with each intermittent exposure to UV radiation leading to accumulation of dermal scaring and ultimately to visible signs of photoageing (2-5). The effect of UV light on induction of MMPs was confirmed also in vitro in fibroblast cultures (6,7). Other studies focusing on mechanism of UV induction of MMPs suggest that UV induced singlet oxygen (a reactive oxygen species) has a direct effect on cells resulting in the production of MMPs (8). Thus antioxidants and specifically those that scavenge singlet oxygen will counteract the UV-stimulated MMP synthesis. However, it cannot be excluded that also other free radical species are involved in stimulation of MMP synthesis. Old cells in culture as well as UV- or sun-exposed skin cells produce higher amounts of MMP. The reduction in MMP-1 activity as a result of the use of a composition of the present invention is thus an indicator of its utility for the maintenance of healthy skin.

Furthermore, the composition of the present invention decreases the formation of advanced glycosylation end products (AGE) by at least 10% as measured under the conditions of Test Method C in comparison to a control, such as by at least 20%, such as at least 30%, 40%, 50%, or 60%, preferably least 70%, particularly at least 80, or 90%, most preferably at least 100 or 110%.

AGE (advanced glycation endproducts, also known as Amadori products) are the result of glycation (glycoxidation), a non-specific binding reaction between proteins and carbohydrates. AGEs accumulate both within individual cells and in the extracellular matrix of tissues consisting of long-lived proteins such as collagen in skin. The AGE-cross-linked proteins are non-functional proteins and tend to aggregate in the extracellular matrix or in the cytoplasm of the cells and are believed to have a deleterious effect on the overall protein synthesis. Initially, an early stage product (Amadori product) is formed when glucose reacts with proteins. This Amadori product then undergoes further rearrangement to form a late-stage brown pigments that can cross-link proteins. After the rearrangement, late-stage products continue to accumulate in long-lived proteins, such as collagen, over long periods of time with high cross-linking of proteins. AGE formation in vivo has been shown to increase with organismal and cellular ageing both in vivo and in vitro. In vivo, the level of AGE accumulation is thought to reflect the serum glucose levels. A critical role in the formation of late stage AGEs is ascribed to oxidation, since glycation itself is a reversible process. Oxidation, however, is responsible for the permanent chemical damage and the loss of functionality of proteins due to permanent cross-links (9). Apart from being non-efficient and having a decreasing effect on overall protein synthesis, AGEs were shown to be chromophores that, after being irradiated with UV light, generate significant amounts of active oxygen radicals (10). Oxidative stress thus contributes to formation of AGEs.

Upon a single dose of exposure to UV radiation (5 J/cm$^2$), the AGE level in non-supplemented control cells increased approximately 20 times compared to non-irradiated control cells. Under the same conditions, the AGE level in cultures supplemented with F increased approximately 40 times, indicating that F has no protective effect on AGE formation upon UV irradiation. Increase in AGE levels in F treated cells was in more dramatic at 7.5 J/cm$^2$. From FIG. 3 it appears that the AGE levels in cells supplemented with FG increased 72 units, which is in the same range as untreated irradiated control cells (a 10% decrease relative to the control).

Figure 3:
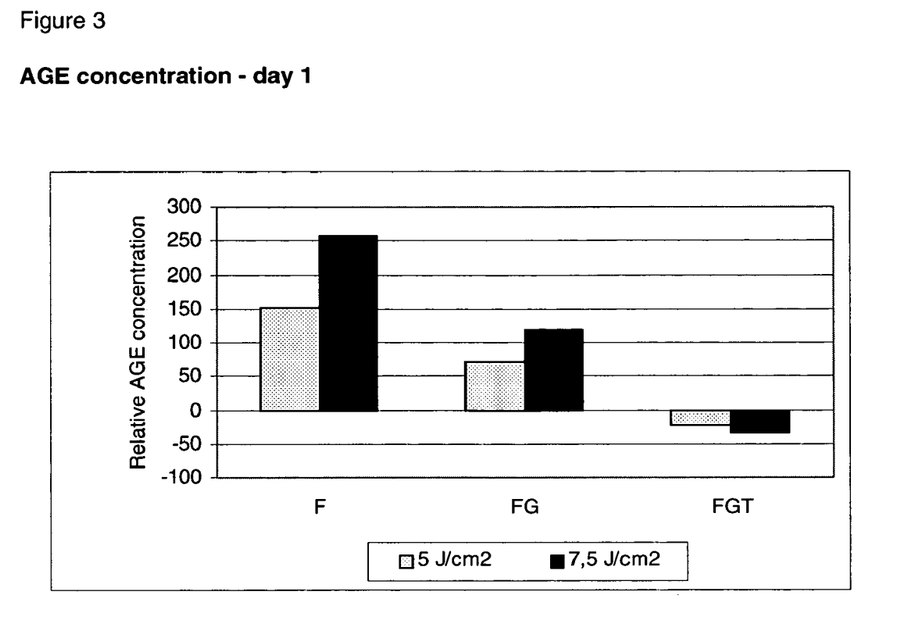
FIG. 3 illustrates the effect of the addition of fish extract (F), fish and grape extract (FG) and fish, grape and tomato extract (FGT) on the formation of advanced glycosylarion products (AGE) in cell cultures.

Remarkably, FGT cells treated cells showed a surprising decrease in AGE level of approximately 22 units relative to non-irradiated cells, which translates to a 120% decrease in AGE concentration relative to non-treated irradiated cells.

Thus compositions of the present invention resulted in improvements in proline incorporation as well as providing beneficial effects in UV exposed cells in terms of MMP-1 activity and AGE formation.

Thus, a further aspect of the invention relates to a composition suitable for the cosmetic treatment of the signs of ageing in skin and for the general maintenance of healthy skin. The signs of ageing may be the result of a number of factors, such as sunlight, time, diet, and other environmental conditions.

Typically, a composition of the present invention comprises 1-80% w/w of compounds extractable from cartilage, weight/weight;

0.1-75% w/w of grape seed extract, weight/weight; and 0.002-25% of lycopene, weight/weight.

Most preferably, a composition of the present invention comprises 27-35%, typically 30-35% cartilage extract, weight/weight
1-10% grape seed extract, such as 3-5% grape seed extract weight/weight; and
0.1 to 5% lycopene, typically 0.2 to 1% lycopene, weight/weight.

The present investigators have prepared suitable compositions comprising 100-110 mg of fish extract
95-105 mg of plant extracts
25-35 mg of Acerola extract
60-90 mg of microcrystalline cellulose
3.5-4.5 mg of silicon dioxide wherein the plant extracts comprise an oligomeric procyanidol and lycopene and the fish extracts comprise a glycosaminoglycan.

A further suitable composition according to the invention comprises 100-110 mg of fish extract
95-105 mg of plant extracts
60-65 mg of inulin
25-35.00 mg of ascorbic acid
10-20 mg of zinc gluconate.
10-15 mg of silicon dioxide wherein the plant extracts comprise an oligomeric procyanidol and lycopene and the fish extracts comprise a glycosaminoglycan.

Thus, a composition of the present invention may further comprise of other components such as further nutritional supplementation such as vitamins, minerals, amino acids and carbohydrates. In a preferred embodiment, the composition further comprises a Vitamin C or an extract containing Vitamin C, such as further comprising Acerola extract.

As stated, the relative and absolute amounts of the constituents are, under the current understanding of the present invention, of great importance to achieving the surprising beneficial effects of the compositions of the present invention. Accordingly, the hydrophilic and the lipophilic antioxidants are preferably present in a wt/wt ratio in the range from about 1:1 to about 200:1, such as from 2:1 to 100:1, in particular from 5:1 to 50:1, especially from 5:1 to 20:1, preferably from 5:1 to 15:1, most preferably about 7:1 to 12:1, such as about 10:1.

Similarly, the cartilage, one or more compounds extractable thereof and the hydrophilic antioxidants are preferably present in a wt/wt ratio in the range from about 1:1 to about 200:1, such as from 2:1 to 100:1, in particular from 5:1 to 50:1, especially from 5:1 to 20:1, preferably from 5:1 to 15:1, most preferably about 7:1 to 12:1, such as about 10:1.

Generally, an important aspect of the present invention relates to a composition wherein the i) cartilage, one or more compounds extractable therefrom, or derivatives thereof, ii) one or more hydrophilic antioxidants, and iii) one or more lipophilic antioxidants are present together in sufficient amounts to suppress MMP-1 activity, to suppress AGE formation or to increase collagen synthesis in human fibroblast cells cultured in vitro.

Similarly, a further important aspect of the present invention relates to composition wherein the i) cartilage, one or more compounds extractable therefrom, or derivatives thereof, ii) one or more hydrophilic antioxidants, and iii) one or more lipophilic antioxidants are present in a ratio suitable to suppress MMP-1 activity, to suppress AGE formation or to increase collagen synthesis in human fibroblast cells cultured in vitro.

In a combination of preferred embodiments, the composition may comprise 0.25-15 mg of lycopene and 2.5-100 mg of grape seed extract, preferably from 0.5-5 mg of lycopene and 5-50 mg of grape seed extract, particularly 0.75-2.5 mg of lycopene and 10-30 mg of grape seed extract, particularly 1-2.5 mg of lycopene and 10-25 mg of grape seed extract.

In a further combination of embodiments, the composition may comprise 1-2.5 mg of lycopene, 5-50 mg of grape seed extract and 50-200 mg of cartilage extract.

The compositions of the invention are for oral administration and may be administered in the form of a solid dosage form such as tablets, powders, granules, capsules, sachets or in a form of a liquid dosage form such as solutions, suspensions, tonics of syrups. Such dosage forms may be prepared in a manner well known in the art of pharmaceutical technology and may contain one or more excipients which may be any of those commonly used within the art. For solid compositions, conventional non-toxic solid excipients may be used including, but not limited to, e.g. pharmaceutical grades of mannitol, lactose, starch, soybean fibre, magnesium stearate, sodium saccharin, talc, cellulose such as microcrystalline cellulose, glucose, saccharose, silicon dioxide, magnesium carbonate or the like. Liquid dosage forms may be obtained by dissolving, dispersing etc. the active components and an optional pharmaceutical adjuvant in an excipient such as water or water-based liquids such a juices, oil or alcohol, in order to form a solution or suspension. If desired, the oral composition according to the invention may also contain minor amounts of additives known in the art such as wetting or emulsifying agents, buffers, or the like. Such dosage forms may be formulated in accordance with principles well known in the art, cf. also e.g. *Remington's Pharmaceutical Sciences*, Mack Publishing Company, Easton, Pa., 15th Edition, 1975; or Martindale, *The Extra Pharmacopeia*, The Royal Pharmaceutical Society of Great Britain, 31th Edition, 1996.

The composition may be such that the lipophilic antioxidant, such as the tomato extract, or an extract comprising lycopene is formulated for normal release and the hydrophilic antioxidant, such as grape seed extract is formulated for delayed or slow release.

Figure 4:
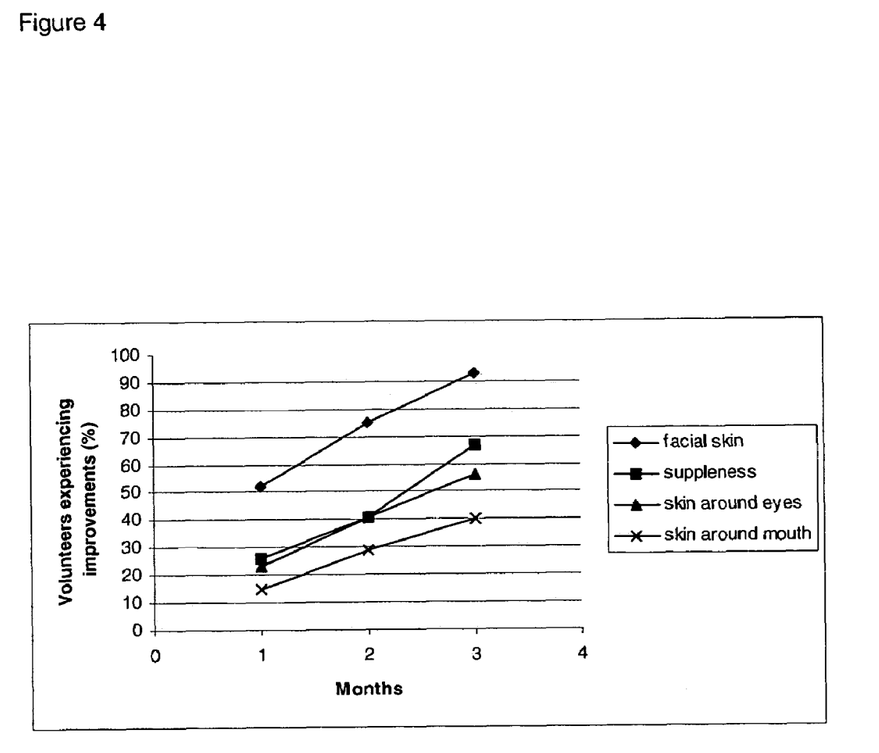
FIG. 4 illustrates ercentage of volunteers experlencing improvements of their skin upon administration of the composition of the invention.

As illustrated from Example 5, the compositions when taken orally have an apparent visible effect on the condition of the skin. FIG. 4 also depicts that those volunteers taking a composition of the present invention noticed improvements in overall skin condition, suppleness, quality of skin around the eyes and skin around the mouth. Thus, the results in Examples 1-4 translated successfully in vivo, the composition seemingly acting systemically when taken orally.

The compositions of the present invention may be for use as an oral cosmetic product, a food or food supplement, a pharmaceutical or a dietetic.

A further aspect of the invention relates to a composition for use in the general maintenance of healthy skin, to delay the onset of the degeneration of skin due to ageing or UV exposure, and for the treatment of the signs of ageing in skin. The compositions of the present invention are suitable in treating ageing skin, skin exposed to sunlight or other forms of UV radiation, dry skin, rough skin, discoloured skin, skin with acne, scared skin, skin with stretch marks, eczema and psoriasis.

A method for the cosmetic or prophylactic treatment of skin against the signs of skin ageing, and damage resulting from exposure to UV radiation comprising the oral administration of a composition defined supra is an important aspect of the invention. Similarly, a method for the cosmetic or prophylactic treatment of ageing skin, skin exposed to sunlight or other forms of UV radiation, dry skin, rough skin, discoloured skin, skin with acne, scarred skin, skin with stretch marks, eczema and psoriasis, comprising the oral administration of a composition defined supra is a further aspect of the invention. The use of a composition defined supra for the preparation of an agent for the preventing or slowing the signs of skin ageing, preventing or lessening the harmful effects of UV radiation exposure, for treating stretch marks, for treating acne, for lessening the symptoms of eczema, for assisting in scar formation and wound healing, for reducing scaring, for lessening the symptoms of psoriasis, or for treating rough, discoloured or dry skin is anticipated.

In these uses, a typical daily dosage for an average adult person is from 55 to 3700 mg of the above defined mixture of cartilage component, hydrophilic antioxidant and lipophilic antioxidant, such as from 70 to 1000 mg. The administration may take place in one daily dose or in divided doses up to four times a day, such as 1, 2, 3 or 4 times, preferably 1 or 2 times daily.

The compositions may be packaged according to principles well known in the art such as in tablet containers, blister packs or bottles. In the event that one of components is sensitive to light which in particular is the case if the lipophilic antioxidant is lycopene, it is advisable to shield the composition from light. In the case of e.g. blister packs, this may suitably be attained if the blister packs are of the well-known type formed from two sheets of aluminium foil and aluminium coated plastic foil, respectively, such as a shaped (forming depressions) sheet of a plastic/aluminium laminate (e.g. a laminate of PVC, aluminium and orientated polyamide foils) and a thin, optionally varnished aluminium foil, respectively.

The invention is illustrated further by the following, non-limiting examples.

EXAMPLES

Example 1

Determination of Effective Concentrations of Hydrophilic Antioxidants, Hydrophobic Antioxidants and Cartilage Extract Various concentrations of grape seed extract (1-200 microg/ml), cartilage extract (0-1000 mg/ml) and tomato extract (0-200 microg/ml) were tested in dose dependent manner in in vitro cultured human skin fibroblast. After evaluation of cell survival and growth rate under all culture conditions, a single optimal concentration for each ingredient was selected.

Method

Working solutions of cartilage extract, grape seed extract and tomato paste containing lycopene were prepared as follows:

Cartilage Solution (40 mg/mL):

200 mg of Fish powder (cartilage extract prepared through enzymatic proteolytic hydrolysis of cartilage, filtration and spray drying of the hydrolysate) were dissolved in 5 mL Hanks Buffered Saline Solution (Hanks) and sterile filtered.

Grape seed Solution (40mg/mL):

200 mg of Grape seed extract (Indena, Milano, Italy) was dissolved in 5 mL Hanks Buffered Saline Solution (Hanks) and sterile filtered.

Tomato Solution (Pre-stock: 100 mg/mL)

Pro-stock: 400 mg of Tomato pasta (containing 40 mg Lycopene) is dissolved in 4 mL of tetrahydrofuran, sterile filtered and stored at −80° C. until use.

Tomato Working Solution (100 µg/mL):

Tomato working solution: Pre-stock is diluted 1:1000 just before use in cell medium DMEM.

Human fibroblast cells were cultured as follows:

10.000 cells/well were seeded in 24-well trays. Cells were allowed to attach overnight before the medium was changed to medium containing different concentrations of cartilage extract (F), grape seed extract (G) and tomato extract (T). Cell medium, DMEM, (10% Foetal Calf Serum, +Glutamine, Penicillin/streptomycin) was changed every second to third day, except for medium containing TE which was renewed everyday. Cells were grown to confluence (37° C., 5% $CO_2$, 95% humidity) and counted every second day using 300 µL Trypsin/EDTA pr.well to detach the cells during a 10 min stay in the incubator at 37° C., where 200 µL were used to count cells/mL.

Cell survival and cell growth were evaluated after up to 15 days.

Cell survival was evaluated by measuring the MTT take-up in cells. The level of uptake corresponds to levels of mitochondrial activity which can be used as a sign of cell viability. The MTT is reduced to a blue coloured compound, formazan, which is detected by UV/VIS absorption at 595 nm with 655 nm as a reference Cell growth was evaluated as a number of cells per culture flask which was counted using an electronic Counter Coulter®.

Results

Figure 1:
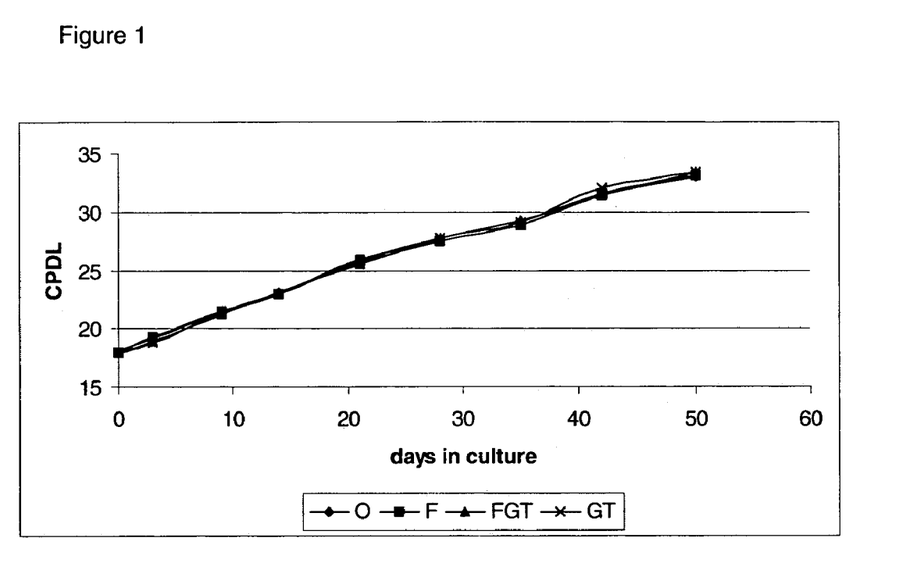
FIG. 1 shows that the monitored cumulative population doubling levels (CPDL) that correspond to number of cell divisions and cell growth are not affected by the ingredients of the compositions of the invention at specified levels.

Cell cultures supplemented with 70 µg/mL of cartilage extract, 10 µg/mL of grape seed extract and 10 µg/mL of tomato extract (=1.0 µg/mL lycopene) provided an optimal environment for cell growth. These concentrations had no toxic effect nor did change the rate of cell divisions. This results was further confirmed by a long term cultivation of fibroblasts in culture medium supplemented with the selected combination (above) over a period of 50 days. The monitored cumulative population doubling levels (CPDL) that correspond to number of cell divisions and cell growth are not affected by the tested ingredients . The results are depicted in Table 1 and FIG. 1.

TABLE 1

| Day | O | F | FGT | GT |
| --- | --- | --- | --- | --- |
| 0 | 18 | 18 | 18 | 18 |
| 3 | 19.17 | 19.34 | 18.87 | 18.8 |
| 9 | 21.4 | 21.52 | 21.28 | 21.32 |
| 14 | 23.08 | 22.93 | 23.05 | 23.02 |
| 21 | 25.65 | 25.87 | 25.59 | 25.67 |
| 28 | 27.53 | 27.57 | 27.73 | 27.78 |
| 35 | 28.88 | 28.88 | 29.2 | 29.15 |
| 42 | 31.45 | 31.54 | 31.4 | 32.03 |
| 50 | 32.98 | 33.14 | 33.42 | 33.39 |

Example 2

Effect of Composition on Collagen Synthesis

In vitro test system was established to test the influence of F, G and T on the synthesis of collagen. The synthesis of collagen was evaluated by measuring the incorporation of radioactive proline ($[^{14}C]$-Proline) into proline-containing proteins, which are mostly regarded to be collagen, where the number of proline residues constitutes over 30% of the total number of amino acids. Various combinations of F, G and T in optimum concentrations determined as described in example 1) were added to the cell medium and the radioactivity of secreted and labelled proteins was measured after 24 hours.

Method

Extracts of F, G and T were produced as in Example 1.

The incorporation of radiolabelled proline in cell human fibroblast cell cultures was carried out as follows (Test Method A): Various combinations of F, G and T were added on the day after seeding and cells were grown to confluence (approx. 1 week). The culture medium was exchanged daily. At confluence, the medium was changed to 0.5 mL radioactive solutions (25 µCi)+2.5 mL medium without F, G or T.

Cells were left in the incubator for the next 24 h and then the medium was collected and subjected to the following procedure to measure the radioactivity:

TCA precipitation: 5 µL of medium was mixed with 20 µL BSA (0.5 g/L) and 1 mL TCA (10%) and left at −20° C. for 30 min. The samples were thawed and put through a nitrocellulose filter to separate free radioactive proline from labelled proteins. The filter was transferred to a tube to which 2.5 mL of scintillation liquid was added. The tube was left in the dark for 1 h after which the radioactivity of the 5 µL sample was measured on the scintillation counter.

Results

Summary of results are shown in Table 2. Cell cultures containing the GT extract resulted in a decrease in the degree of incorporation of proline compared to the control: 3.6% incorporation compared with 4.8% in the control, a 25% decrease. Cell cultures containing the FT extract had no significant influence on the proline incorporation, since the degree of incorporation was 5.0% compared with 4.8% in the control, a 4% increase, only. Cell cultures containing the FG extract resulted in a small increase in the degree of incorporation of proline: 5.5% incorporation, a 45% increase compared to the control.

Cell cultures containing the F extract resulted in an increase in the degree of incorporation of proline: 6.2% incorporation, a 29% increase. FGT extracts, however, surprisingly resulted in a dramatic 75% increase in proline incorporation: (8.4% of proline incorporated).

In this type of experiments, a difference above 30% is considered significant.

TABLE 2

| Treatment | Activity in dpm | Activity in µCi Output | % incorporated proline | Result relative to control |
|---|---|---|---|---|
| GT | 4516 | 0.0015 | 3.6 | 25% decrease |
| Control | 5787 | 0.0020 | 4.8 | |
| FT | 4516 | 0.0021 | 5.0 | 4% increase |
| FG | 5137 | 0.0023 | 5.5 | 14.6% increase |
| F | 5787 | 0.0026 | 6.2 | 29% increase |
| FGT | 7738 | 0.0035 | 8.4 | 75% increase |

Example 3

Effect of Composition on Human Fibroblasts upon UV Exposure

UVA exposure is responsible for a number of degenerative changes in skin that lead to the visible signs of ageing (photo-ageing). The potential protective effect of F, G and T extracts and their combinations against UV induced damage was tested by monitoring biochemical markers associated with photoageing (levels of MMP-1 and AGEs) in skin fibroblast culture upon UV irradiation.

Cell cultures of human fibroblast were exposed to one dose of UVA radiation each day for 4 consecutive days. Two different doses were used (5 and 7.5 J/cm$^2$) and corresponds to the maximal dose tolerated by cells before cell death occur.

The cell culture was supplemented with various combinations of F, G and T (F, FG, FT, GT and FGT) using the optimum concentrations of F, G and T (as determined and described in Example 1) and the MMP-1 activity and AGE formation was measured after 1 day and 4 days.

Methods

Extracts were produced as described in Example 1.

Culturing of cells was carried out as follows:

Cells with a given passage were changed to a medium containing the combinations of F, G and T treatment. At confluency they were split 1:4 to obtain 4 flasks for each treatment. At confluency one (1:4 split) or two (1:2 split) were serially passaged to four new flasks.

UVA irradiation of cell culture was carried out as follows

An UVA dose was produced using a 6x Philips 40W UVA Cleo Performance tubes. A Hagner UVA meter was used to measure the dose in W/m$^2$ and to calculate the needed time of exposure to achieve a wanted dose of 5, 7.5, 10 and 15 J/cm$^2$. Preliminary experiments show that the optimum dose of irradiation not causing cell death was 7.5 J/cm$^2$.

Determination of MMP-1 activity (endogeneous activity plus latent levels) was performed using a commercially available test system from APBiotech, Code RPN 2629 (Test Method B).

Determination of AGEs was based on ELISA technique (Test Method C):

Day 1: Microplates were coated with 50 ng of AGE/well, diluted in carbonate buffer, overnight at +4° C.

Day 2: The wells were washed 4 times with PBST (PBS and 0.05% Tween 20) and then blocked in 200 µL/well of PBS-milk (6%) for 2 h at room temperature (RT). Wells were then washed 4 times with PBST, before, firstly, the addition of 50 µL AGE standard (20-20.000 units/well) or 50 µL of sample (50 µg protein/mL) to the wells, followed by 50 µL of the AGE polyclonal antibody (dilution ¹⁄₁₀₀₀). The plate was placed at fast agitation for 2 h at RT. The wells were washed 4 times with PBST before the addition of the second antibody (Polyclonal Rabbit, HRP, dilution ¹⁄₁₀₀₀) with 50 µL/well and placed on agitation for 2 h at RT. Finally, the wells were washed 4 times in PBST, before the addition of the substrate (1 OPD tablet/3 mL ddH$_2$O+¹⁄₁₀₀₀ (v/v) of hydrogen peroxide (35%) with 100 µl/well. The plate was left in a dark place, and after the development of appropriate colour, the reaction was stopped by the addition of 50 µL H$_2$SO$_4$ (1M). Plate absorbance was read at 490 nm (ref. 655 nm)

Results

Figure 2A:
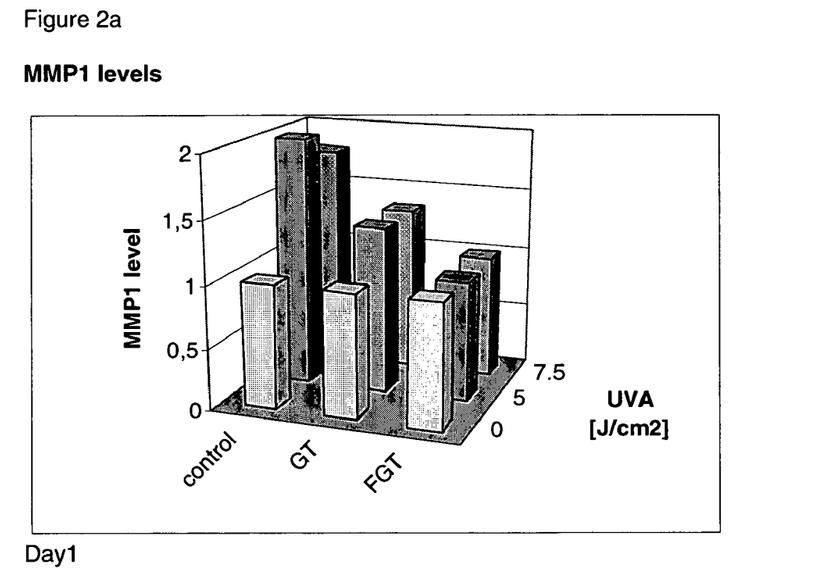
FIG. 2a shows the potential protective effect of grape and tomato extract (GT) and fish, grape and tomato extract (FGT) on degenerative changes in skin at day 1 of UV exposure, as measured by the level of matrix metalloproteinase-1 (MMP-1)
Figure 2B:
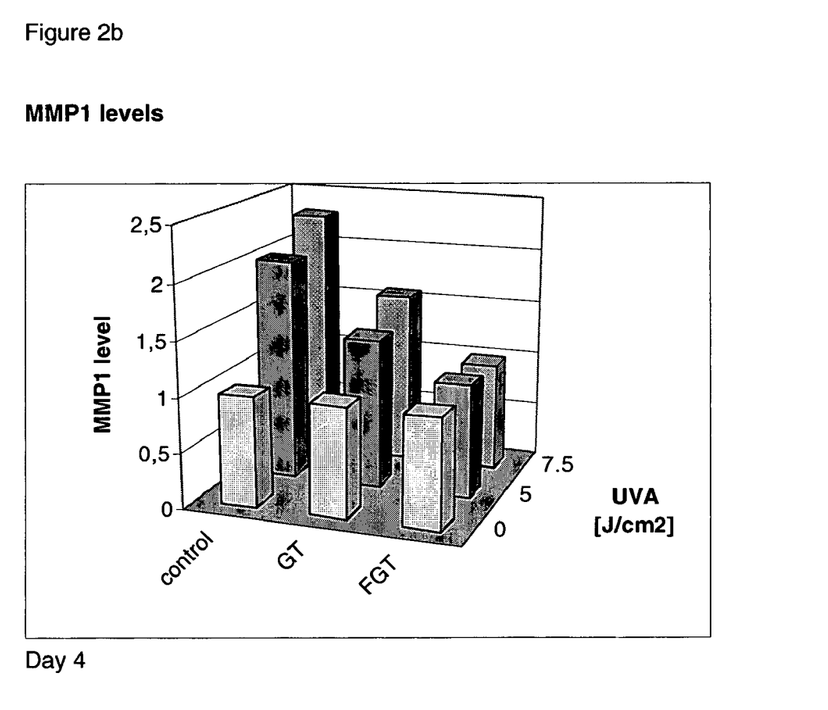
FIG. 2b shows the potential protective effect of grape and tomato extract (GT) and fish, grape and tomato extract (FGT) on degenerative changes in skin at day 4 of UV exposure, as measured by the level of matrix metalloproteinase-1 (MMP-1).

Results for MMP-1 activity and AGE formation are shown in FIGS. 2 and 3, respectively.

I. MMP-1 Activity

UVA irradiation was shown to induce MMP-1 activity in untreated cells (control) in both the Day 1 and Day 4 studies, thereby confirming the capability of MMP1 induction in cultured fibroblasts by UVA. MMP-1 activity of the control cells approximately doubled during the photo-ageing process Cells treated with GT showed a 34% and 58% increase on Days 1 and 4, respectively. Conversely, MMP-1 activity was induced in cells supplemented with F. MMP-1 activity approximately tripled and quadrupled after UV exposure on Day 1 and Day 4, respectively.

Surprisingly, combining F with GT to form FGT resulted in a no increase in MMP-1 activity in UV exposed cells. Thus FGT treated cells have half of the MMP-1 activity as the control cells under identical conditions.

TABLE 3

| | Day 1 | | |
|---|---|---|---|
| | 0 J/cm$^2$ | 5 J/cm$^2$ | 7.5 J/cm$^2$ |
| control | 1 | 2.01 | 1.80 |
| GT | 1 | 1.34 | 1.34 |
| FGT | 1 | 0.97 | 0.99 |

TABLE 3a

| | Day 4 | | |
|---|---|---|---|
| | 0 J/cm$^2$ | 5 J/cm$^2$ | 7.5 J/cm$^2$ |
| control | 1 | 2.02 | 2.3 |
| GT | 1 | 1.37 | 1.58 |
| FGT | 1 | 1.04 | 0.99 |

II. AGE Formation

Results are depicted in FIG. 3 and Table 4. Upon a single dose of exposure to UV radiation (5 J/cm$^2$), the AGE level in non-supplemented control cells increased proximately 20 times compared to non-irradiated control cells. Under the same conditions, the AGE level in cultures supplemented with F increased 40 times, which shows that F has no protective effect on AGE formation upon UV irradiation. From FIG. 3 it appears that the AGE levels in cells supplemented with FG increased 72 units, which is in the same range as untreated irradiated control cells (a 10% decrease relative to the control).

Remarkably, FGT cells treated cells showed a surprising decrease in AGE level of approximately 22 units relative to non-irradiated cells, which translates to a 120% decrease in AGE concentration relative to non-treated irradiated cells.

Thus compositions of the present invention resulted in improvements in proline incorporation as well as providing beneficial effects in UV exposed cells in terms of MMP-1 activity and AGE formation.

TABLE 4

| | 5 J/cm$^2$ | 7.5 J/cm$^2$ |
|---|---|---|
| control | 80.06 | 67.88 |
| F | 152.72 | 258.21 |
| FG | 72.04 | 118.58 |
| FGT | −21.94 | −34.92 |

Example 4

Compositions according to the invention were prepared using the following ingredients mixed in the stated proportions (the amounts given are per final dosage unit):

Lycopene is sensitive to oxidation, mixing of granulate and handling, compressing of tablets, storage of tablets and packaging in alu-alu-blister cards are all performed under protective nitrogen.

Composition 1 (Tablet code SF)
- 105 mg of cartilage extract (prepared through enzymatic proteolytic hydrolysis of cartilage, filtration and spray drying of the hydrolysate);
- 100 mg plant extracts (containing ca. 1.5 mg lycopene extracted from tomatoes and ca. 14 mg flavonoids extracted from grape seeds, the remainder being soy fiber, tomato oil and silicon dioxide; Alextan® from Indena, Milano, Italy);
- 30 mg Acerola extract (containing ca. 7.5 mg ascorbic acid, the remainder being Acerola constituents and maltodextrin);
- 66 mg microcrystalline cellulose
- 4 mg silicon dioxide (particle size 2.4-3.6 µm).

The mixing was performed in a Lodige mixer for 6 minutes. The powder mixture was compressed into tablets with a weight of 305 mg.

Composition 2 (Tablet code SF-1)
- 105 mg of cartilage extract (prepared through enzymatic proteolytic hydrolysis of cartilage, filtration and spray drying of the hydrolysate);
- 100 mg plant extracts (containing ca. 1.5 mg lycopene extracted from tomatoes and ca. 14 mg flavonoids extracted from grape seeds, the remainder being soy fiber, tomato oil and silicon dioxide; Alextan® from Indena, Milano, Italy);
- 30 mg Acerola extract (containing ca. 7,5 mg ascorbic acid, the remainder being Acerola constituents and maltodextrin);
- 81 mg microcrystalline cellulose
- 4 mg silicon dioxide (particle size 2.4-3.6 µm).

The mixing was performed in a Lödige mixer for 6 minutes. The powder mixture was compressed into tablets with a weight of 320 mg.

Composition 3 (Tablet Code SS)
- 105 mg of cartilage extract (prepared through enzymatic proteolytic hydrolysis of cartilage, filtration and spray drying of the hydrolysate);
- 100 mg plant extracts (containing ca. 1.5 mg lycopene extracted from tomatoes and ca. 14 mg flavonoids extracted from grape seeds, the remainder being soy fiber, tomato oil and silicon dioxide; Alextan® from Indena, Milano, Italy);
- 62 mg inulin
- 30 mg ascorbic acid
- 15 mg zinc gluconate
- 13 mg silicon dioxide (particle size 2.4-3.6 µm).

The mixing was performed in a Lödige mixer for 6 minutes. The powder mixture was compressed into tablets with a weight of 325 mg.

Typical composition
FE: 105 mg
GE: 13.75 mg
TE: 14.38 mg (from this lycopene is 10% =1.44 mg)

Example 5

The composition in Example 1 was tested in a consumer test to determine consumers' perception of changes in the skin.

129 volunteers entered a three-month study and took two tablets daily containing the composition in Example 1. They recorded their skin appearance and quality before entering the test. After 1, 2, and 3 months of supplementation they evaluated changes in skin appearance and quality according to the following codes: 0—condition unchanged, 1—slightly improved, 2—improved, 3—much improved.

FIG. 4 shows the results of the evaluation of the parameters "overall skin condition", "suppleness", quality of "skin around eyes" and "skin around mouth". Improvements are percentage of volunteers experiencing improvements.

REFERENCES

1. Emonard, H. & Grimaud, J. A. Matrix metalloproteinases. A review. Cell Mol. Biol. 36,131-153 (1990).
2. Fisher, G. J. et al. Pathophysiology of premature skin aging induced by ultraviolet light. N. Engl. J. Med. 337, 419-1428 (1997).
3. Fisher, G. J. & Voorhees, J. J. Molecular mechanisms of photoaging and its prevention by retinoic acid: ultraviolet irradiation induces MAP kinase signal transduction cascades that induce Ap-1-regulated matrix metalloproteinases that degrade human skin in vivo. J. Investig. Dermatol. Symp. Proc. 3, 61-68 (1998).
4. Fisher, G. J., Talwar, H. S., Lin, J. & Voorhees, J. J. Molecular mechanisms of photoaging in human skin in vivo and their prevention by all-trans retinoic acid. Photochem. Photobiol. 69,154-157 (1999).
5. Hase, T. et al. Histological increase in inflammatory infiltrate in sun-exposed skin of female subjects: the possible involvement of matrix metalloproteinase-1 produced by inflammatory infiltrate on collagen degradation. Br. J. Dermatol. 142, 267-273 (2000).
6. Petersen, M. J., Hansen, C. & Craig, S. Ultraviolet A irradiation stimulates collagenase production in cultured human fibroblasts. J. Invest Dermatol. 99, 440-444 (1992).
7. Scharffetter, K. et al. UVA irradiation induces collagenase in human dermal fibroblasts in vitro and in vivo. Arch. Dermatol. Res. 283, 506-511 (1991).
8. Wlaschek, M., Briviba, K. & Stricklin, P. Singlet Oxygen May Mediate Ultraviolet A-Induced Synthesis of Interstitial Collagenase. J. Invest Dermatol. 104,194-198 (1995).
9. Fu, M. X., Knecht, K. J., Thorpe, S. R. & Baynes, J. W. Role of oxygen in cross-linking and chemical modification of collagen by glucose. Diabetes 41 Suppl 2, 42-48 (1992).
10. Masaki, H., Okano, Y. & Sakurai, H. Generation of active oxygen species from advanced glycation end-products (AGEs) during ultraviolet light A (UVA) irradiation and a possible mechanism for cell damaging. Biochim. Biophys. Acta 1428, 45-56 (1999).

The invention claimed is:

1. A method of increasing collagen synthesis or lessening the decrease in collagen synthesis in the dermis comprising the oral administration to a human in need thereof of a composition comprising:
   i) at least one glycosaminoglycan found in cartilage enzymatic hydrolysate, or a synthetic form of at least one glycosaminoglycan;
   ii) at least one polyphenolic, hydrophilic antioxidant found in grape seed; or synthetic form of at least one polyphenolic hydrophilic antioxidant and esters thereof; and
   iii) lycopene; and
   wherein the weight ratio of the at least one polyphenolic, hydrophilic antioxidant to the 1 lycopene is about 1:1 to about 200:1 and the weight ratio of the at least one glycosaminoglycan to the at least one polyphenolic, hydrophilic antioxidant is about 1:1 to about 200:1.

2. A method according to claim 1, wherein the at least one polyphenolic, hydrophilic antioxidant is obtained from a grape seed extract.

3. A method according to claim 2, wherein the grape seed extract is obtained by using organic solvents.

4. A method according to claim 3, wherein said grape seed extract comprises up to 25% w/w of catechin, epicatechin or gallic acid; up to 90% w/w of epicatechin dimer, trimer or tetramer, or gallates thereof, or up to 10% w/w of epicatechin pentamer, hexamer or heptamer, or gallates thereof.

5. A method according to claim 3, wherein the grape seed extract is obtained by using the organic solvents, evaporating the solvents, re-dissolving a residue in water, and filtering and drying a filtrate.

6. A method according to claim 3, wherein the organic solvents are selected from the group consisting of acetone, ethyl acetate and mixtures thereof.

7. A method according to claim 1, wherein said at least one polyphenolic, hydrophilic antioxidant is obtained from at least one natural source.

8. A method according to claim 1, wherein said at least one polyphenolic, hydrophilic antioxidant comprises an oligomeric procyanidol.

9. A method according to claim 1, wherein said lycopene is obtained from a tomato variety.

10. A method according to claim 1, wherein said lycopene is obtained from a tomato extract.

11. A method according to claim 1, wherein said composition, further comprises a carotenoid comprising β-carotene, γ-carotene, δ-carotene, zeaxanthin, cryptoxanthine, lutein, xanthophyll, or a combination thereof.

12. A method according to claim 11, wherein the composition comprises less than 0.025% β-carotene by weight.

13. A method according to claim 1, wherein the composition comprises said lycopene in an amount of 0.1 to 5% wt/wt.

14. A method according to claim 1, wherein the composition comprises 0.25-15 mg of the lycopene and further comprises 2.5-100 mg of a grape seed extract.

15. A method according to claim 14, wherein said composition comprises 0.75-2.5 mg of the lycopene and 10-30 mg of the grape seed extract.

16. A method according to claim 1 wherein said composition comprises 1-2.5 mg of the lycopene, and further comprises 5-50 mg of a grape seed extract and 50-200 mg of a cartilage enzymatic hydrolysate.

17. A method according to 1, wherein said composition further comprises Acerola extract.

18. A method according to claim 1, wherein said composition is in a form for oral administration comprising tablets, powders, granules, capsules, sachets, solutions, suspensions, tonics of syrups, or a combination thereof.

19. A method according to claim 1, wherein said glycosaminoglycan is from a cartilage enzymatic hydrolysate obtained by enzymatic proteolytic cleavage of a cartilage.

20. A method according to claim 19, wherein said cartilage is selected from the group consisting of bovine cartilage, porcine cartilage, shark cartilage, squid cartilage, chicken cartilage and salmon cartilage.

21. A method according to claim 19, wherein the composition further comprises a cartilage enzymatic hydrolysate and a grape seed extract, and the cartilage enzymatic hydrolysate and the grape seed extract are present in a weight/weight ratio in the range of from about 5:1 to 15:1.

22. A method according to claim 21, wherein said composition comprises 1-2.5 mg of the lycopene, 5-50 mg of the grape seed extract and 50-200 mg of the cartilage enzymatic hydrolysate.

23. A method according to claim 19, wherein the composition further comprises a cartilage enzymatic hydrolysate and a grape seed extract, and the cartilage enzymatic hydrolysate and the grape seed extract are present in a weight/weight ratio of about 1:2 to 2:1.

24. A method according to claim 1, wherein said glycosaminoglycan is from a shark cartilage enzymatic hydrolysate obtained by enzymatic proteolytic cleavage of said shark cartilage.

25. A method according to any one of claims 1 and 19, wherein said glycosaminoglycan comprises chondroitin ester, a keratan ester, hyaluronic acid or an ester thereof, a dermatan ester, heparin or a heparan ester.

26. A method according to claim 25, wherein said composition comprises 1-2.5 mg of the lycopene, and further comprises 5-50 mg of a grape seed extract and 50-200 mg of a cartilage enzymatic hydrolysate.

27. A method according to any one of claims 1 and 19, wherein the composition further comprises a cartilage enzymatic hydrolysate, and the cartilage enzymatic h,/drolysate and the lycopene are present in a weight/weight ratio of about 1:2 to 2:1.

28. A method according to claim 1, wherein the weight ratio of the at least one polyphenolic, hydrophilic antioxidant to lycopene is 2:1 to 100:1.

29. A method according to claim 1, wherein the weight ratio of the at least one glycosaminoglycan to the at least one polyphenolic, hydrophilic antioxidant is 2:1 to 100:1.

30. A method according to claim 1, which includes a treatment of skin against the signs of skin ageing, and damage resulting from exposure to UV radiation.

31. A method according to claim 1, wherein the weight ratio of the at least one polyphenolic, hydrophilic antioxidant to lycopene is 5:1 to 50:1.

32. A method according to claim 1, wherein the weight ratio of the at least one polyphenolic, hydrophilic antioxidant to lycopene is 5:1 to 20:1.

33. A method according to claim 1, wherein the weight ratio of the at least one polyphenolic, hydrophilic antioxidant to lycopene is 5:1 to 15:1.

34. A method according to claim 1, wherein the weight ratio of the at least one polyphenolic, hydrophilic antioxidant to lycopene is 7:1 to 12:1.

35. A method according to claim 1, wherein the weight ratio of the at least one polyphenolic, hydrophilic antioxidant to lycopene is about 10:1.

36. A method according to claim 1, wherein the weight ratio of the at least one glycosaminoglycan to the at least one polyphenolic, hydrophilic antioxidant is 5:1 to 50:1.

37. A method according to claim 1, wherein the weight ratio of the at least one glycosaminoglycan to the at least one polyphenolic, hydrophilic antioxidant is 5:1 to 20:1.

38. A method according to claim 1, wherein the weight ratio of the at least one glycosaminoglycan to the at least one polyphenolic, hydrophilic antioxidant is 5:1 to 15:1.

39. A method according to claim 1, wherein the weight ratio of the at least one glycosaminoglycan to the at least one polyphenolic, hydrophilic antioxidant is 7:1 to 12:1.

40. A method according to claim 1, wherein the weight ratio of the at least one glycosaminoglycan to the at least one polyphenolic, hydrophilic antioxidant is about 10:1.

* * * * *

UNITED STATES PATENT AND TRADEMARK OFFICE
CERTIFICATE OF CORRECTION

| | | |
|---|---|---|
| PATENT NO. | : 7,435,432 B2 | Page 1 of 2 |
| APPLICATION NO. | : 09/853635 | |
| DATED | : October 14, 2008 | |
| INVENTOR(S) | : Bengt Krister Olson | |

It is certified that error appears in the above-identified patent and that said Letters Patent is hereby corrected as shown below:

Please add in claim 1, column 17, third paragraph ii) the language "or esters thereof" after "grape seed" and change "and esters thereof" to "or esters thereof".
Please add in claim 1, column 17, fourth paragraph iii) the language "or esters thereof" after both instances of "hydrophilic antioxidant".

Please correct in claim 17, "Acerola" to "Acerola"
Please correct in claim 27, "h,/drolysate" to "hydrolysate"
Please add in claim 31, the language "or esters thereof" after "antioxidant".
Please add in claim 32, the language "or esters thereof" after "antioxidant".
Please add in claim 33, the language "or esters thereof" after "antioxidant".
Please add in claim 34, the language "or esters thereof" after "antioxidant".
Please add in claim 35, the language "or esters thereof" after "antioxidant".
Please add in claim 36, the language "or esters thereof" after "antioxidant".
Please add in claim 37, the language "or esters thereof" after "antioxidant".
Please add in claim 38, the language "or esters thereof" after "antioxidant".
Please add in claim 39, the language "or esters thereof" after "antioxidant".
Please add in claim 40, the language "or esters thereof" after "antioxidant".

Please add claim 41, "A method according to claim 2, wherein the grape seed extract and lycopene are in weight/weight ratio of about 5:1 to 15:1."
Please add claim 42, "A method according to claim 1, wherein the composition consists essentially of:
i.) at least one glycosaminoglycan found in cartilage enzymatic hydrolysate, or a synthetic form of at least one glycosaminoglycan;

UNITED STATES PATENT AND TRADEMARK OFFICE
CERTIFICATE OF CORRECTION

PATENT NO. : 7,435,432 B2
APPLICATION NO. : 09/853635
DATED : October 14, 2008
INVENTOR(S) : Bengt Krister Olson It is certified that error appears in the above-identified patent and that said Letters Patent is hereby corrected as shown below:

ii.) at least one polyphenolic, hydrophilic antioxidant found in grape seed or esters thereof; or synthetic form of at least one polyphenolic hydrophilic antioxidant or esters thereof; and
iii) lycopene."

Signed and Sealed this

Twenty-ninth Day of September, 2009

David J. Kappos
*Director of the United States Patent and Trademark Office*

UNITED STATES PATENT AND TRADEMARK OFFICE
CERTIFICATE OF CORRECTION

PATENT NO.        : 7,435,432 B2
APPLICATION NO.   : 09/853635
DATED             : October 14, 2008
INVENTOR(S)       : Bengt Krister Olson It is certified that error appears in the above-identified patent and that said Letters Patent is hereby corrected as shown below:

Please add in claim 1, column 17, line 50, --or esters thereof-- after "grape seed" and line 51, change "and esters thereof" to --or esters thereof--.
Please add in claim 1, column 17, lines 54 and 57, --or esters thereof-- after "hydrophilic antioxidant".

Column 18, please correct in claim 17 line 38, "Acerola" to --Acerola--.
Column 19, please correct in claim 27 line 11, "h,/drolysate" to --hydrolysate--.
Column 19, please add in claim 31 line 24, the language --or esters thereof-- after "antioxidant".
Column 19, please add in claim 32 line 27, the language --or esters thereof-- after "antioxidant".
Column 20, please add in claim 33 line 2, the language --or esters thereof-- after "antioxidant".
Column 20, please add in claim 34 line 5, the language --or esters thereof-- after "antioxidant".
Column 20, please add in claim 35 line 8, the language --or esters thereof-- after "antioxidant".
Column 20, please add in claim 36 line 13, the language --or esters thereof-- after "antioxidant".
Column 20, please add in claim 37 line 16, the language --or esters thereof-- after "antioxidant".
Column 20, please add in claim 38 line 20, the language --or esters thereof-- after "antioxidant".
Column 20, please add in claim 39 line 23, the language --or esters thereof-- after "antioxidant".
Column 20, please add in claim 40 line 26, the language --or esters thereof-- after "antioxidant".

UNITED STATES PATENT AND TRADEMARK OFFICE
CERTIFICATE OF CORRECTION

PATENT NO. : 7,435,432 B2
APPLICATION NO. : 09/853635
DATED : October 14, 2008
INVENTOR(S) : Bengt Krister Olson

It is certified that error appears in the above-identified patent and that said Letters Patent is hereby corrected as shown below:

Column 20, line 27, add Claims 41 and 42,
claim 41, --A method according to claim 2, wherein the grape seed extract and lycopene are in weight/weight ratio of about 5:1 to 15:1.--.
claim 42, --A method according to claim 1, wherein the composition consists essentially of:
i.) at least one glycosaminoglycan found in cartilage enzymatic hydrolysate, or a synthetic form of at least one glycosaminoglycan;
ii.) at least one polyphenolic, hydrophilic antioxidant found in grape seed or esters thereof; or synthetic form of at least one polyphenolic hydrophilic antioxidant or esters thereof; and
iii) lycopene.--.

This certificate supersedes the Certificate of Correction issued September 29, 2009.

Signed and Sealed this

Twenty-seventh Day of October, 2009

David J. Kappos
*Director of the United States Patent and Trademark Office*